US006544538B1

(12) United States Patent
Caine

(10) Patent No.: US 6,544,538 B1
(45) Date of Patent: Apr. 8, 2003

(54) INSECTICIDAL COMPOSITION

(75) Inventor: Gavin Ronald Caine, South Wentworthville (AU)

(73) Assignee: Reckitt Benckiser (Australia) PTY Limited, West Ryde (AU)

( * ) Notice: Subject to any disclaimer, the term of this patent is extended or adjusted under 35 U.S.C. 154(b) by 0 days.

(21) Appl. No.: 09/254,106

(22) PCT Filed: Sep. 5, 1997

(86) PCT No.: PCT/AU97/00581

§ 371 (c)(1),
(2), (4) Date: Apr. 12, 1999

(87) PCT Pub. No.: WO98/09515

PCT Pub. Date: Mar. 12, 1998

(30) Foreign Application Priority Data

Sep. 5, 1996 (GB) ............................................... 9618572

(51) Int. Cl.⁷ ........................ A01N 25/00; A01N 25/28; A01N 33/26; A01N 33/02; A01N 25/02
(52) U.S. Cl. ...................... 424/405; 424/408; 424/410; 424/DIG. 11; 424/451; 424/457; 424/489; 424/520; 424/543; 514/565; 514/963; 514/965
(58) Field of Search ................................ 424/405, 408, 424/DIG. 11, 410, 451, 457, 489, 520, 543; 514/565, 963, 965

(56) References Cited

U.S. PATENT DOCUMENTS

| | | | | |
|---|---|---|---|---|
| 4,834,977 A | * | 5/1989 | Kohama et al. | 424/405 |
| 4,936,901 A | | 6/1990 | Surgent et al. | 71/92 |
| 5,178,872 A | * | 1/1993 | Ohtsubo et al. | 424/408 |
| 5,229,122 A | * | 7/1993 | Chadwick et al. | 424/408 |
| 5,300,293 A | * | 4/1994 | Minagawa et al. | 424/405 |
| 5,607,684 A | * | 3/1997 | Lew et al. | 424/405 |
| 5,690,951 A | * | 11/1997 | Lew et al. | 424/410 |

FOREIGN PATENT DOCUMENTS

| | | | |
|---|---|---|---|
| EP | 0 238 184 A1 | 9/1987 | ........... A01N/25/28 |
| EP | 0 368 285 A1 | 5/1990 | ........... A01N/25/28 |
| EP | 0 427 991 A1 | 5/1991 | ........... A01N/25/28 |
| EP | 0 518 821 A2 | 12/1992 | ............ A01M/1/20 |
| EP | 0 548 901 A1 | 6/1993 | ........... A01N/25/28 |
| GB | 1 561 901 | 3/1980 | ........... A01N/25/00 |
| GB | 2 231 797 A | 11/1990 | ........... A01N/25/08 |
| GB | 2 237 741 A | 5/1991 | ........... A01N/25/02 |

OTHER PUBLICATIONS

Copy of GB Patent Office Search Report for GB Application No. 9618572.3 dated Jan. 15, 1997.
Supplementary European Search Report for EP 97 93 7361 dated Jun. 2, 2000.
Derwent Abstract Accession No. 96–065420/07, JP 07–324004 A, Dec. 12, 1995, abstract.
Derwent Abstract Accession No. 90–080951/11, JP 02–03610 A, Feb. 6, 1990, abstract.
Derwent Abstract Accession No. 88–297292/42, JP 63–218605 A, Sep. 12, 1988, abstract.
Copy of International Search Report for PCT/AU97/00581 dated Sep. 23, 1997.

* cited by examiner

*Primary Examiner*—Frederick Krass
*Assistant Examiner*—Clinton Ostrop
(74) *Attorney, Agent, or Firm*—Fish & Richardson P.C.

(57) ABSTRACT

An insecticidal bait composition which is particularly useful against social insects, such as cockroaches and ants is disclosed. The bait composition comprises a solid or semi-solid bait matrix including a food material for an insect and one or more non-microencapsulated insecticides in an amount effective to act essentially as a primary kill agent and one or more microencapsulated insecticides, excluding pyrethroids, in an amount effective to act essentially as a secondary kill agent, the non-microencapsulated insecticide and microencapsulated insecticide being the same or different.

9 Claims, No Drawings

INSECTICIDAL COMPOSITION

This is a national stage application filed under 35 U.S.C. 371 of PCT/AU97/00581, which was filed Sep. 5, 1997.

TECHNICAL FIELD

The present invention relates to insecticidal bait compositions for use against insects having social contact, in particular to bait compositions that exhibit both a primary kill and an effective secondary kill.

BACKGROUND ART

Insecticidal bait compositions are generally materials that will be eaten by insects of at least one species and will either directly kill insects, affect the fecundity of the insect so that the insect population is reduced in the next generation, or alter the behaviour of the insect in a manner that will bring about their destruction.

It is usual for bait compositions to contain one or more insecticides in combination with one or more food materials and optionally an attractant. Note that some materials will function both as a food source and as an attractant.

Bait compositions are presented in a variety of forms including tablets, pastes, gels and other semi-solid preparations. Given the toxic nature of the insecticide(s) included in the bait composition, for safety reasons in use they are frequently held in a container or housing that only allows insect access. For this reason, it is important to ensure that baits are sufficiently effective both in delivery of insecticides and attractancy to the insects, The art is replete with insecticides together with a wide variety of bait compositions. Many of these insecticides are effective providing that they are consumed by insects and therefore in use can bring about a high rate of insect mortality.

Notwithstanding the effectiveness of many insecticides, in order to bring about a substantial reduction in total insect population, it is necessary to maximize the attractiveness of baits so as to maximise the proportion of insect population that will be brought into direct contact with bait compositions.

One can also provide bait compositions which are capable of transmission between insects so as to bring about a greater reduction in insect population. The effectiveness of such compositions is not directly dependent upon each insect consuming the bait composition at its source.

In the art, the extent to which an insect population is reduced by direct contact with the bait composition is referred to as "primary kill". Similarly, the extent to which an insect population is reduced as a result of transmission of bait composition between insects is referred to as "secondary kill".

The present inventor has recognised that in the case of insects having social contact such as cockroaches and in the case of social isects such as ants. it is evident that bait compositions exhibiting both effective primary and secondary kills will bring about a greater reduction in insect population than a composition exhibiting a primary kill effectiveness alone.

Surprisingly, the present inventor has found that an insecticidal bait composition exhibiting both effective primary and secondary kills may be achieved through the use of a combination of two insecticides where one insecticide is substantially active as a primary kill agent and a second microencapsulated insecticide is substantially active as a secondary kill agent.

As used in this specification, all concentrations are % w/w unless otherwise specified.

DISCLOSURE OF THE INVENTION

Accordingly, the present invention provides an insecticidal bait composition comprising a solid or semi-solid bait matrix including a food material for an insect and one or more non-microencapsulated insecticides in an amount effective to act essentially as a primary kill agent and one or more microencapsulated insecticides, excluding pyrethroids, in an amount effective to act essentially as a secondary kill agent, the non-microencapsulated insecticide and microencapsulated insecticide being the same or different.

In another aspect, the present invention provides a method of killing insects that have social contact comprising exposing an insect population to an insecticidal bait composition comprising a solid or semi-solid bait matrix including a food material for an insect and one or more non-microencapsulated insecticides in an amount effective to act essentially as a primary kill agent and one or more microencapsulated insecticides, excluding pyrethroids, in an amount effective to act essentially as a secondary kill agent, the non-microencapsulated insecticide and microencapsulated insecticide being the same or different.

In a further aspect, the present invention provides for the use of effective amounts of one or more non-microencapsulated insecticides in combination with one or more microencapsulated insecticides, excluding pyrethroids, ill a solid or semi-solid bait matrix including a food material for an insect, the non-microencapsulated insecticide and microencapsulated insecticide being the same or different and acting respectively essentially as a primary kill agent and a secondary kill agent.

Without wishing to be bound by theory, it is thought that secondary kill occurs as a result of one or more of the following mechanisms:

(a) Faeces of insects that have already consumed a bait include residual insecticide which is ingested by other insects.

(b) Insects that have died as a result of consuming a bait are cannibalised by other insects or perhaps by eating or digesting secretions from the dead or dying insects.

(c) Social contact between insects where particles of bait composition including insecticide are passed.

(d) As a result of preening and insect movement, particles of bait composition are distributed over a surface allowing for insects moving over the surface to subsequently consume the bait particles.

Bait Matrix

The bait matrix will include one or more food materials for the insect. In addition, the bait matrix may comprise a variety of other components including insect attractant(s), fillers and materials as required to prepare the composition in a suitable form.

Amongst the food materials that may be used are: lipids, carbohydrates, proteins, essential oils, water, spices and mixtures thereof. Preferred food materials comprise short chain polysaccharides including starches such as are present in flours, particularly corn flour. Other preferred food materials include fats and oils such as fully hydrogenated fatty acids, preferably fully hydrogenated peanut oil as well as oils such as soy bean oil which also acts as an attractant for cockroaches.

Other fatty materials that may be used include esters, waxes, soaps, phospholipids such as lecithin, glycolipids, turpenes and steroids.

Preferred carbohydrates and protein materials include cereal products such as bran and wheat germ; vegetable products such as potato flour, dehydrated vegetables; sugars, starches and complex carbohydrates including monosaccharides and cellulosic materials; dried yeast, egg powder and insect derived materials such as silkworm pupa, eggs and body parts.

In general terms, the bait matrix may comprise from 85 to 99.9% w/w of the composition. Preferably the bait matrix will be in a concentration of 90 to 99.9% w/w, most preferably 95 to 99.8% w/w.

As noted above, it is desirable to include insect attractant(s) in order to ensure that contact between insect and bait composition is maximised. Amongst the attractants that may be used are pheromones, yeast extracts, complex foods and volatile materials such as flavour essences and food derivatives including fenugreek, herbs and spices.

When insecticides are themselves repellant in nature to insects, preferably an attractant as taught and disclosed in International Patent Application No PCT/AU96/00374 (U.S. 08/665877) now abandoned is used.

Preferably, attractants will be included in the composition in a concentration of 0.01% to 5% w/w.

Desirably, the attractants will also function as food materials. Likewise, it is desirable that the food materials also function as attractants.

As mentioned above, bait compositions generally may be presented in a variety of forms. The bait compositions of this invention may be presented as tablets, pastes, gels and other solid and semi-solid forms. Of these, pastes, gels and semi-solid forms are preferred. Particularly preferred are the semi-solid compositions taught and disclosed in AU-A-9218651, the contents of which are included herein by way of cross reference. The advantage of such compositions is that they are substantially non-crumbling, cohesive and non-particulate in character. This means that when used in a typical bait housing, as taught and disclosed in AU-B-9220748, the composition will not be released into the enviroment. This is particularly important in relation to the safety of children who otherwise may gain access to relatively toxic materials.

Accordingly, compositions that are particulate in character, such as dusts, powders and granules are not suitable forms for the compositions of the invention.

It is also desirable to include a preservative since growth of microorganisms on the composition may function to repel insects. Amongst the preservatives that may be used are sorbic acid and its salts, Dowicil® (Dow-Elanco) and methyl- and propyl-parabens.

In compositions that include fats and/or oils, it may be appropriate to include an antioxidant such as butylated hydroxytoluene or butylated hydroxyanisole.

Non-micrenicapsulated Insecticide

The one or more non microencapsulated insecticides may be chosen from a wide range of insecticides known in the art including pyrethroids, avermectinis, hydrarnethylnon, fluorinated suifluoramides, organophosphates including diazinon and chlorpyrifos, pyrazoles such as fipronil, carbamates and hydrazones. A preferred insecticide is chlorpyrifos.

The insecticide(s) chosen will generally be incorporated in a concentration of from 0.01 to 5% w/w preferably from 0.02 to 3% w/w, most preferably from 0.04 to 1% w/w.

Microencapsulated Insecticide

The one or more microencapsulated insecticides may be chosen from a wide range of insecticides known in the art, excluding pyrethroids, but including avermectins, hydramethylnon, sulfluoramid, organophosphates including diazinon and chlorpyrifos, carbamates and hydrazones. A preferred insecticide is chlorpyrifos.

A variety of microencapsulation methods and compositions which are well known in the art may be applied to these insecticides. In choosing a microencapsulation composition, it is important to ensure that the composition is compatible with the bait matrix, that is the insecticide is not released into the composition.

A further consideration is that in accordance with the theory of the mechanism by which secondary kill may occur, a further desirable property is that the microencapsulated material has some resistance to digestion by the insect.

Generally, microencapsulated insecticide(s) will be incorporated in a concentration of from 0.01% to 5% w/w, preferably 0.02 % to 3% w/w, most preferably 0.05% to 1.0% w/w, especially 0.05% to 0.5% w/w. Note that these concentrations are with respect to the active insecticide contained in the microcapsules.

The compositions of the invention are effective against social insects, particularly cockroaches and ants, especially cockroaches.

MODES FOR CARRYING OUT THE INVENTION

In order to better understand the nature of the invention, an example will now be described:

EXAMPLE 1

| INGREDIENTS | % W/W | MAIN FUNCTION |
|---|---|---|
| Peanut Oil Fully Hydrogenated | 55.0 | *Food, |
| Soyabean Oil | 18.0 | *Food, attractant |
| Fenugreek | 1.0 | Attractant |
| Potassium Sorbate | 0.15 | Preservative |
| Sorbic Acid | 0.050 | Preservative |
| Cornflour | 24.694 | *Food |
| Chlorpyrifos | 0.353 | Insecticide |
| Empire 20 | 0.753 | Microencapsulated insecticide |
| TOTAL | 100.00 | |

*These ingredients also function to maintain the composition in semi-solid form.

Ingredients and Availability

| | |
|---|---|
| Peanut Oil Fully Hydrogenated | Peanut Oil (Meadow Lea Foods) |
| Soyabean Oil | Soyabean Oil (Meadow Lea Foods) |
| Fenugreek | Fenugreek (Waters Trading Pty Ltd) |
| Potassium Sorbate | Potassium Sorbate (Amcor Trading) |
| Sorbic Acid | Sorbic Acid (Amcor Trading) |
| Cornflour | Cornflour (Starch Australasia) |
| Chlorpyrifos | Chlorpyrifos 99% (Dow-Elanco) |
| Empire 20 | Microencapsulated Chlorpyrifos 20% w/w (Dow-Elanco) |

Example 1 may be prepared as follows:

The soyabean oil is heated and then the peanut oil added until the two are well mixed. The remaining ingredients are added to the hot oil until the mixture becomes light brown and flowable. Once flowable, the composition is filled into a well of a suitable bait housing. On cooling, the bait composition solidifies to a semi-solid such that it is retained in the well within the housing.

Efficacy

In order to demonstrate the efficacy of the compositions of the invention, a second example containing the same insecticides and in the same concentration as the insecticides in Example 1 was tested as set out below.

Evaluation of Secondary kill
Bioassay Method
1. Thirty mixed sex adult cockroaches were placed in each of 9 large plastic arenas (base area 2,820 $cm^2$ and height 46 cm). The sides of the arenas were coated with fluon to prevent escape. There were four replicates (arenas) for each of the bait treatments and one for the control.
2. The cockroaches were provided with a harbourage in the form of a rolled piece of corrugated cardboard, a water source and a dog food pellet. The positioning of the harbourage, food and water was the same for each arena.
3. The cockroaches were allowed to acclimatise overnight and any dead were replaced the next morning.
4. One cockroach bait was placed in the same position in each of the treatment arenas. There were four arenas for each of the two bait treatments.
5. No bait was placed in the control arena.
6. The baits were left in each arena until approximately 50% of the cockroaches were knocked down. The baits were then removed.
7. A further 20 adults were then added to each of the arenas except for the control arena. These adults previously housed in a small container, had been fed the requisite bait for approximately 4 hours. The number of dead adult cockroaches out of the total number of 50 were noted at the time of nymph introduction.
8. In the control arena, twenty adult cockroaches, killed by freezing were added to ensure the presence of dead adults alone, were not killing the nymphs.
9. Twenty mid-stage nymphs were then added to each arena including the control.
10. The arenas were checked for mortality of both adult and nymph cockroaches. Deaths were noted every day for the first 7 days and then every other day up to day 15. Dead adult cockroaches were left in the arenas. Dead nymphs were removed immediately following scoring.
11. The test was conducted separately against two species of cockroach—*Blatella germanica* and *Periplaneta americana*.

Evaluation of Primary Kill
Bioassay Method
1. In each of the trays, 100 cockroaches (25 adults and 75 mid to late stage nymphs) were placed. They were left for one day to acclimatise and any dead cockroaches were replaced.
2. The baits were introduced into all but one of the trays (day 0) and left for 21 days. There were 2 baits provided for every tray. Each tray consisted of a melamine square tray of sides 1.8 m×1.8 m with 20 cm high walls. The upper part of the wall was provided with electrical strip which prevented cockroaches escaping.
3. No baits were provided in the control tray.
4. There were 4 trays for each of the baits and one tray for the control.
5. Alternative food sources were provided in every tray. The food sources consisted of oats and peanut butter—one location of each. There was 1 water dispenser in each tray. There were also four harbourages in the form of rolled corrugated cardboard. The location of food; water, harbourages and baits were the same for all of the trays.
6. The number of dead cockroaches were scored at daily intervals for the first 7 days and every other day up to day 21.
7. All dead cockroaches were removed immediately after scoring.
8. The test was conducted separately against two species of cockroach—*Blatella germanica* and *Periplaneta americana*.

Results

The results for both primary kill are shown in Tables 1 and 2, whilst results for secondary kill are shown in Tables 3 and 4. For comparative purposes, a typical cockroach bait composition containing chlorpyrifos but no microencapsulated insecticide was included in the tests.

TABLE 1

Primary Kill
Species: *Blattella germanica*

| | | Percentage Kill | |
| --- | --- | --- | --- |
| Day | Control | Comparative | Example 1 |
| 1 | 0.5 | 10 | 12.5 |
| 2 | 0.5 | 23.5 | 31.5 |
| 3 | 1 | 35.2 | 43.2 |
| 4 | 1 | 45.8 | 53.5 |
| 5 | 1 | 54 | 61.5 |
| 6 | 1.5 | 60 | 69.0 |
| 7 | 1.5 | 65 | 73.8 |
| 9 | 2.5 | 69.8 | 79.2 |
| 11 | 2.5 | 75 | 84.0 |
| 13 | 2.5 | 81.8 | 89.8 |
| 15 | 2.5 | 86 | 93.5 |
| 17 | 3 | 89.5 | 96.5 |
| 19 | 4.5 | 90.2 | 97.5 |
| 21 | 5.5 | 92.2 | 99.0 |

TABLE 2

Primary Kill
Species: *Periplaneta americana*

| | | Percentage Kill | |
| --- | --- | --- | --- |
| Day | Control | Comparative | Example 1 |
| 1 | 0 | 15.8 | 8.0 |
| 2 | 0 | 40.2 | 37.8 |
| 3 | 0 | 53 | 59.0 |
| 4 | 0 | 59.5 | 65.8 |
| 5 | 0 | 69.5 | 70.5 |
| 6 | 0 | 77.5 | 79.2 |
| 7 | 1 | 82.2 | 83.5 |
| 9 | 2 | 86.5 | 90.0 |
| 11 | 4 | 90.8 | 93.8 |
| 13 | 4 | 93.2 | 96.8 |
| 15 | 4 | 96.2 | 98.2 |
| 17 | 4 | 97 | 99.2 |
| 19 | 4 | 98 | 99.5 |
| 21 | 5 | 98.8 | 99.5 |

TABLE 3

Secondary Kill
Species: *Blattella germanica*

| | | Percentage Kill | |
| --- | --- | --- | --- |
| Day | Control | Comparative | Example 1 |
| 1 | 0 | 3.8 | 3.8 |
| 2 | 0 | 6.2 | 15.0 |
| 3 | 0 | 11.2 | 22.5 |
| 4 | 5 | 15 | 31.2 |
| 5 | 5 | 16.2 | 36.2 |
| 6 | 5 | 18.8 | 43.8 |
| 7 | 5 | 18.8 | 47.5 |
| 9 | 10 | 18.8 | 48.8 |

TABLE 3-continued

Secondary Kill
Species: *Blattella germanica*

| | Percentage Kill | | |
|---|---|---|---|
| Day | Control | Comparative | Example 1 |
| 11 | 10 | 20 | 48.8 |
| 13 | 10 | 22.5 | 51.2 |
| 15 | 10 | 23.8 | 52.5 |

TABLE 4

Secondary Kill
Species: *Periplaneta americana*

| | Percentage Kill | | |
|---|---|---|---|
| Day | Control | Comparative | Example 1 |
| 1 | 0 | 13.8 | 21.2 |
| 2 | 0 | 40 | 47.5 |
| 3 | 0 | 41.2 | 60.0 |
| 4 | 0 | 43.8 | 65.0 |
| 5 | 0 | 56.2 | 76.2 |
| 6 | 0 | 62.5 | 81.2 |
| 7 | 0 | 68.8 | 83.8 |
| 9 | 0 | 76.2 | 87.5 |
| 11 | 0 | 77.5 | 90.0 |
| 13 | 0 | 82.5 | 91.2 |
| 15 | 0 | 83.8 | 91.2 |

It is evident from these test results that the example of the invention demonstrated a superior secondary kill whilst maintaining an effective primary kill against both species of cockroaches.

Furthermore, it should be noted that the insecticide chlorpyrifos is considerably lower in price as compared with insecticides such as averinectins which are klown to exert a secondary kill in non-microencapsulated form.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A method of killing insects that have social contact comprising:
feeding an insect population an insecticidal bait composition comprise a solid or semi-solid bait matrix including a food material for an insect and said insecticidal bait composition having dispersed within:
  (a) as a primary kill agent an effective amount of one or more non-microexncapsulated insecticides and
  (b) as a secondary kill agent an effective amount of one or more microencapsulated insecticides, excluding pyrethroids, wherein the non-microencapsulated insecticide and microencapsulated insecticide may be the same or different characterized in that
said insecticidal bait composition, when ingested by an insect is effective in killing said insect, and,
said insecticidal bait composition after having been ingested by said insect remains in a killing-effective amount within the body of the ingesting insect, or in the excrement of the ingesting insect such that a killing-effective amount of said secondary kill agent is available and ingestible by further insects who are killed due to the ingestion of the secondary kill agent.

2. The method according to claim 1 wherein the bait matrix is present in a concentration of 85 to 99.9% w/w of the insecticidal bait composition.

3. The method according to claim 1 wherein the non-microencapsulated insecticide is present in an amount of 0.01 to 5% w/w of the insecticidal bait composition.

4. The method according to claim 1 wherein the microencapsulated insecticide is present in an amoumt of 0.01 to 5% w/w of the insecticidal bait composition.

5. The method according to claim 1 wherein the microencapsulated insecticide is pot in an amount of 0.02 to 3% w/w of the insecticidal bait composition.

6. The method according to claim 1 wherein the microencapsulated insecticide is selected from the group consisting of avermectins, hydramethylnon, fluorinated sulfluoramides, organophosphates, diazinon, chlorpyrifos, carbamates, pyrazoles, fipronil and hydrazones.

7. The method according to claim 1 wherein the non-microencapsulated insecticide is chlorpyrifos.

8. The method according to claim 1 wherein the microencapsulated insecticide is chlorpyrifos.

9. The method according to claim 1 wherein the insect is a cockroach.

* * * * *